(12) United States Patent
Kaspar et al.

(10) Patent No.: US 9,205,080 B2
(45) Date of Patent: Dec. 8, 2015

(54) METHODS OF TREATING KERATIN HYPERPROLIFERATION DISORDERS USING MTOR INHIBITORS

(75) Inventors: Roger Louis Kaspar, Santa Cruz, CA (US); Robyn Patricia Hickerson, Santa Cruz, CA (US)

(73) Assignee: Transderm, Inc., Salt Lake City, UT (US)

( * ) Notice: Subject to any disclaimer, the term of this patent is extended or adjusted under 35 U.S.C. 154(b) by 1603 days.

(21) Appl. No.: 11/985,850

(22) Filed: Nov. 16, 2007

(65) Prior Publication Data

US 2008/0207672 A1   Aug. 28, 2008

Related U.S. Application Data

(60) Provisional application No. 60/866,161, filed on Nov. 16, 2006.

(51) Int. Cl.
*A61K 31/4745* (2006.01)
*A61K 31/436* (2006.01)

(52) U.S. Cl.
CPC .................................. *A61K 31/4745* (2013.01)

(58) Field of Classification Search
CPC ................................................ A61K 31/4745
USPC ......................................................... 514/291
See application file for complete search history.

(56) References Cited

U.S. PATENT DOCUMENTS

| | | | |
|---|---|---|---|
| 5,286,730 A * | 2/1994 | Caufield et al. ................ | 514/291 |
| 5,994,081 A | 11/1999 | Tang et al. | |
| 6,221,843 B1 | 4/2001 | Tang et al. | |
| 2002/0015702 A1* | 2/2002 | Burkly et al. .............. | 424/142.1 |
| 2003/0170630 A1* | 9/2003 | Alsobrook et al. ................ | 435/6 |
| 2005/0031547 A1* | 2/2005 | Tamarkin et al. ................ | 424/45 |
| 2005/0192261 A1* | 9/2005 | Jost-Price et al. ............. | 514/171 |
| 2007/0031509 A1* | 2/2007 | Sundae ......................... | 424/638 |
| 2008/0064668 A1* | 3/2008 | Uskokovic et al. ........... | 514/167 |

FOREIGN PATENT DOCUMENTS

| | | |
|---|---|---|
| EP | 0 703 985 | 10/2003 |
| WO | WO 00/10516 | 3/2000 |
| WO | WO 2005/091891 A2 | 10/2005 |

OTHER PUBLICATIONS

Ashton, Gabrielle, et al, "Prenatal Diagnosis for Inherited Skin Diseases," Clinics in Dermatology, vol. 18, pp. 643-648 (2000).*
Watson, Christopher, et al, "Sirolimus and Everolimus: Inhibitors of Mammalian Target of Rapamycin in Liver Transplantation," Transplantation Reviews, vol. 20, pp. 104-114 (2006).*
Leigh et al "Keratins (K16 and K17) as markers of keratinocyte hyperproliferation in psoriasis in vivo and in vitro" (Br J Dermatology: Oct. 1995, vol. 133, pp. 501-511; Abstract only).*
Bowden et al "Mutation of a type II keratin gene (K6a) in pachyonychia congenital" (Nat Genet: Jul. 1995, vol. 10, pp. 363-365; Abstract only).*
Smith et al. J. Invest. Dermatol. Symp. Proc 10: 21-30, 2005.*
Macron (RNAi, startup believes siRNAs can treat extremely rare skin disorder [pp. 4-5, published online Sep. 30, 2005, retrieved on Jul. 5, 2008].*
Hickerson et al. (Ann. N. Y. Acad. Sci., Oct. 2006 vol. 1082: pp. 56-61).*
www.rnai.news.com, pp. 4 and 5 (published Sep. 30, 2005).*
Leigh et al., Keratins (K16 and K17) as markers of keratinocyte hyperproliferation in psoriasis in vivo and in vitro. Br. J. Dermatology, Oct. 1995, vol. 133, pp. 501-511; abstract.
Bowden et al., Mutation of a type II keratin gene (K6a) in pachyonychia congenita, Nat. Genet., Jul. 1995, vol. 10, pp. 363-365, Abtract.
H.B.J. Jefferies, et al., Rapamycin selectively represses translation of the "polypyrimidine tract" mRNA family, Proc. Natl. Acad. Sci. USA, Cell Biology, vol. 91, pp. 4441-4445, May 1994.
Nissim Hay and Nahum Sonenberg, Upstream and downstream of mTOR, Genes & Development 18:1926-1945 2004 http://www,genesdev.org/cgi/doi/10.1101/gad.1212704.
Harold B.J.Jefferies, et al., Rapamycin Suppresses 5'Top Mrna Translation Through Inhibition Of P70s6k, The EMBO Journal vol. 16 No. 12 pp. 3693-3704, 1997.
Roger L. Kaspar, et al., A Regulatory Cis Element and a Specific Binding Factor Involved in the Mitogenic Control of Murine Ribosomal Protein L32 Translation, The Journal of Biological Chemistry and Molecular Biology, Inc. vol. 267, No. 1, Issue of Jan. 5, pp. 508-514,1992.
Kenzo Takahashi, et al. Cloning and Characterization of Multiple Human Genes and cDNAs Encoding Highly Related Type II Keratin 6 Isoforms,Tthe Journal of Biological Chemistry, vol. 270, No. 31, Issue of Aug. 4, pp. 18581-18592, 1995.
E. Petroulakis, et al., mTOR signaling: implications for cancer and anticancer therapy; British Journal of Cancer (2006) 94, 195-199.
Dror Avni, et al., Vertebrate mRNAs with a 5'-Terminal Pyrimidine Tract Are Candidates for Translation Repression in Quiescent Cells: Characterization of the Translation cis-Regulatory Element, Molecular and Cellular Biology, Jun. 1994, p. 3822-3833.
A.D. Ormerod, et al. Treatment of psoriasis with topical siromlimus:preclinical development and a randomized, double-blind trial, British Journal of Dermatology 2005 152, pp. 758-764.
Naohiro Terada et al., Rapamycin selectively inhibits translation of mRNAs encoding elongation factors and ribosomal proteins, Proc. Natl. Acad. Sci USA, vol. 91, pp. 11477-11481, Nov. 1994.
Jianfeng Zhu, Differential transaltion of Top mRNA in rapamycin-treated human B lymphocytes, Dept. of Chemistry and Biochemistry, Brigham Young University, Provo, UT Usa May 2003.

* cited by examiner

*Primary Examiner* — Catherine S Hibbert
(74) *Attorney, Agent, or Firm* — Thorpe North & Western, LLP

(57) ABSTRACT

A method of treating or preventing keratin hyperproliferation skin disorders is set forth. The method includes the administration of an mTOR inhibitor to a subject afflicted with the hyperproliferation disorder. The mTOR inhibitor can be administered to the subject via any means known in the art including oral, topical, and transdermal administration.

13 Claims, 6 Drawing Sheets

FIG. 2

K6a (chr12: 51173237-51173343, see also NM_00554 and AC_000055)
SEQ. ID. No. 1 – TCCA█████GCTGCTGCCCGAGCCTGATTCCTAGTCCTGCTTC
TCTTCCCTCT█TCCTCCAGCCTCTCACACTCTCCTCAGCTCTCTCATCTCCTGGAAC
C███GCCAGCACATCCACCACCATCAGGAG K16 (chr17: 37022464-37022578, see also NW_926828 and NM_005557.2)
SEQ. ID. No. 2 – TGCA█████AGGTCTCTGGGGTTGGAGGCAGCC█CAGCACGCTC
TCAGCCTTCCTGAGCACCTTTCCTTCTTTCAGCCAACTGCTCACTCGCTCACCTCC
CTCCTTGGCACC███ACCACCTGCAGCCGCCAG K6b (chr12:51132127-51132232, see also nM_005557 and AC_000055)
SEQ. ID. No. 3 – TCCA█████GCTGCTACTGGAGTCCGATTCCTCGTCCTGCTTC
TCCTCCCTCT█GCCTCCAGCCTCTCACACTCTCCTAAGCCCTCTCATCTCCTGGAA
CC███GCCAGCACATCCACCACCATCAGGAGC K17 (chr17:37034285-37034389, see also NM_000422 and NW_926828)
SEQ. ID. No. 4 – GGCC█████GGAAGCGGGCGAACCCCGGCAGCCCTACACAAC
TTGGGGCCCCT█TCCTCTCCAGCCCTTCTCCTGTGTGCCTGCCTCCTGCCGCCGCC
ACC███ACCACCTCCATCCGCCAGTTCACCTCCT K5 (chr12:51200345-51200477, see also BC02492 and NW_925395)
SEQ. ID. No. 5 – GGGA█████GGGGGCATCACCGTTCCTGGGTAACAGAGCCAC
█TTCTGCGTCCTGCTGAGCTCTGTTCTCTCCAGCACCTCCCAACCCACTAGTGCCT
GGTTCTCTTGCTCCACCAGGAACAAGCCACC███

K14 (chr17:36996610-36996706, see also NM_000526 and NW_926828)
SEQ. ID. No. 6 – CGAG█████GCACTCGCATCCCTTTCCAATTT█CCCGAGCACC
TTCTCTTCACTCAGCCAACTGCTCGCTCGCTCACCTCCCTCCTGCACC███ACTAC
CTGCAGCCGCCAGTTCACCTCCTCCAGCTCC Lamin A/C (chr1:154351089-154351337, see also L12399 and NM_170707)
SEQ. ID. No. 7 – GACC█████GAGCCTTTGCCCCGGCGTCGGTG█CTCAGTGTTCG
CGGGAGCGCCGCACCTACACCAGCCAACCCAGATCCCGAGGTCCGACAGCGCCC
GGCCCAGATCCCCACGGAGCCAGCCGGCCGGCGCACTCCGACTCCGAGCAGTCT
CTGTCCTTCGACCCGAGCCCCGCGCCCTTTCCGGGACCCCTGCCCCGCGGGCAGC
GCTGCCAACCTGCCGGCC███GAGACCCCGTCCCAGCGGC Translation elongation factor 1A (EF1A) (EF362804 and D28375)
SEQ. ID. No. 8 – ACCG█████GTGCAGTAGTCGCCGTGAACGTT█TTTTTCGCA
ACGGGTTTGCCGCCAGAACACAGGTGTCGTGAAAACTACCCCTAAAAGCCAAA█
█GGAAAGGAAAAGAC ■ - Transcriptional initiation start site (predicted)   ■ - TATA box ☐ - Polypyrimidine tract   ■ - Translational initiation start site FIG. 3
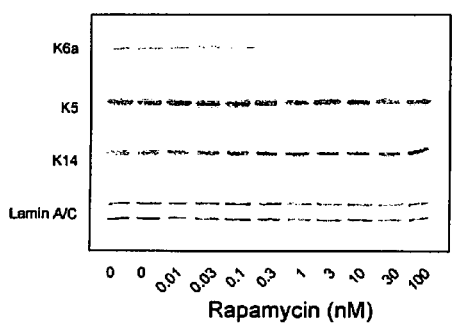
A.
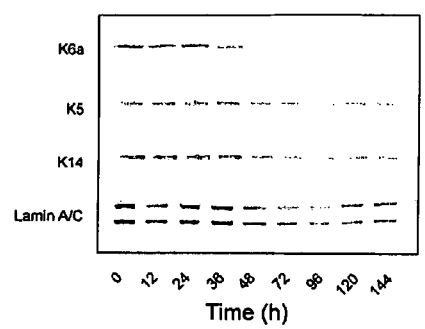
B.
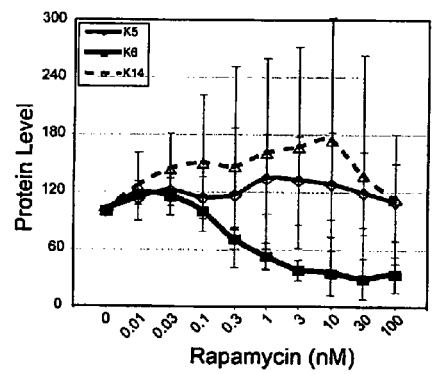
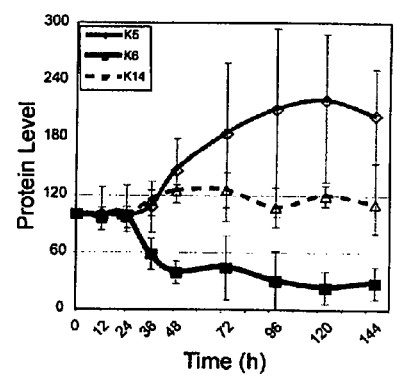

FIG. 4B
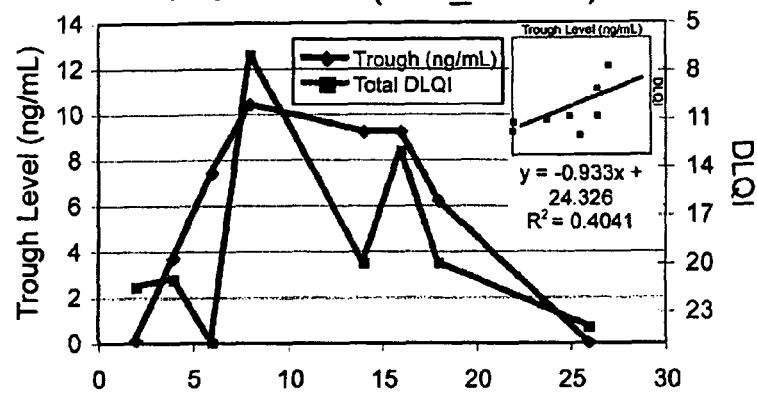
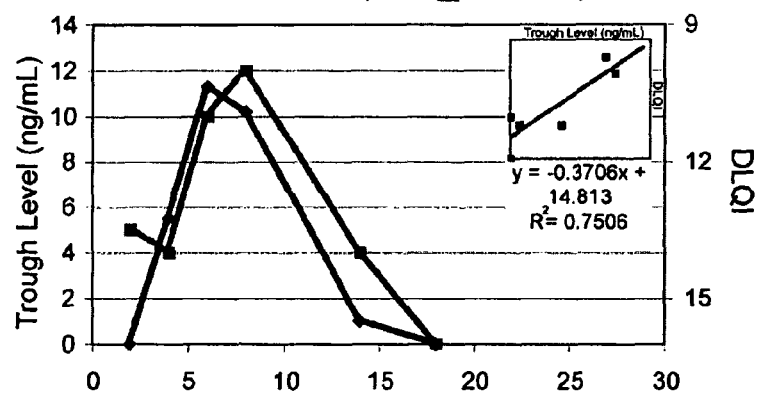
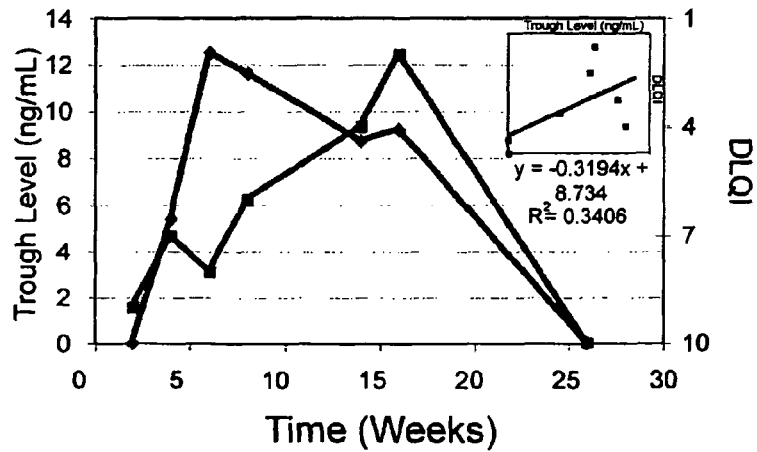

```
                              SEQUENCE LISTING

<160> NUMBER OF SEQ ID NOS: 8

<210> SEQ ID NO 1
<211> LENGTH: 133
<212> TYPE: DNA
<213> ORGANISM: Homo sapiens

<400> SEQUENCE: 1
tccatatata agctgctgcc cccagcctga ttcctagtcc tgcttctctt ccctctctcc      60
tccagcctct cacactctcc tcagctctct catctcctgg aaccatggcc agcacatcca    120
ccaccatcag gag                                                       133

<210> SEQ ID NO 2
<211> LENGTH: 133
<212> TYPE: DNA
<213> ORGANISM: Homo sapiens

<400> SEQUENCE: 2
tcgatataaa ggtctctggg gttggaggca gccacagcac gctctcagcc ttcctgagca     60
cctttccttc tttcagccaa ctgctcactc gctcacctcc ctccttggca ccatgaccac    120
ctgcagccgc cag                                                       133

<210> SEQ ID NO 3
<211> LENGTH: 133
<212> TYPE: DNA
<213> ORGANISM: Homo sapiens

<400> SEQUENCE: 3
tccatatata agctgctact ggagtccgat tcctcgtcct gcttctcctc cctctcgcct     60
ccagcctctc acactctcct aagccctctc atctcctgga accatggcca gcacatccac    120
caccatcagg agc                                                       133

<210> SEQ ID NO 4
<211> LENGTH: 133
<212> TYPE: DNA
<213> ORGANISM: Homo sapiens

<400> SEQUENCE: 4
ggcctataaa ggaagcgggc gaaccccggc agccctacac aacttggggc ccctctcctc     60 tccagcccctt ctcctgtgtg cctgcctcct gccgccgcca ccatgaccac ctccatccgc   120
cagttcacct cct                                                       133

<210> SEQ ID NO 5
<211> LENGTH: 133
<212> TYPE: DNA
<213> ORGANISM: Homo sapiens

<400> SEQUENCE: 5
gggataaaaa gggggcatca ccgttcctgg gtaacagagc caccttctgc gtcctgctga     60
gctctgttct ctccagcacc tcccaaccca ctagtgcctg gttctcttgc tccaccagga    120
acaagccacc atg                                                       133
```

```
<210> SEQ ID NO 6
<211> LENGTH: 133
<212> TYPE: DNA
<213> ORGANISM: Homo sapiens

<400> SEQUENCE: 6
cgagtataaa gcactcgcat cccttttccaa tttacccgag caccttctct tcactcagcc      60
aactgctcgc tcgctcacct ccctcctctg caccatgact acctgcagcc gccagttcac     120
ctcctccagc tcc                                                        133

<210> SEQ ID NO 7
<211> LENGTH: 266
<212> TYPE: DNA
<213> ORGANISM: Homo sapiens

<400> SEQUENCE: 7
gacctattag agcctttgcc ccggcgtcgg tgactcagtg ttcgcgggag cgccgcacct      60
acaccagcca acccagatcc cgaggtccga cagcgcccgg cccagatccc cacgcctgcc     120
aggagcaagc cgagagccag ccggccggcg cactccgact ccgagcagtc tctgtccttc     180
gacccgagcc ccgcgccctt tccgggaccc ctgccccgcg ggcagcgctg ccaacctgcc     240
ggccatggag accccgtccc agcggc                                          266

<210> SEQ ID NO 8
<211> LENGTH: 133
<212> TYPE: DNA
<213> ORGANISM: Homo sapiens

<400> SEQUENCE: 8
accgtatata agtgcagtag tcgccgtgaa cgttcttttt cgcaacgggt ttgccgccag      60
aacacaggtg tcgtgaaaac taccoctaaa agccaaaatg ggaaaggaaa agactcatat     120
caacattgtc gtc                                                        133
```

METHODS OF TREATING KERATIN HYPERPROLIFERATION DISORDERS USING MTOR INHIBITORS

This application claims the benefit of U.S. Provisional Application No. 60/866,161, filed Nov. 16, 2006.

BACKGROUND

Keratin hyperproliferation disorders afflict a large number of individuals. Most of these disorders have no cure and the treatments primarily focus on amelioration of the symptoms of the disorders. As such research continues to discover methods of treatment for these diseases.

SUMMARY

The present invention is drawn to a method of treating or preventing keratin hyperproliferation skin disorders in a subject. The method includes administering to the subject a therapeutically effective amount of an mTOR inhibitor.

BRIEF DESCRIPTION OF THE DRAWINGS

FIG. 2—shows a comparison of the sequences of the 5' untranslated regions (UTRs) of the common keratins including the inducible keratins K6a, K6b, K16 and K17. The location and presence of terminal oligopyrimidine (TOP) elements in the inducible keratins are shown in yellow. The lack of a TOP element does not mean it does not exist but rather may reflect the lack of proper identification of the 5' end of the messenger RNA. For example, immediately upstream of the human K6b 5' terminal "c" residue is the sequence cttctcctc-cctctg (see NCBI accession #L42584), suggesting it is also a TOP mRNA and the sequence listed may not contain the full-length 5' UTR. It should be noted that the regulatory pyrimidine element need not be at the terminus of the 5'UTR in order to be functional (see Kasper et al., J. Biol. Chemistry, 1992).

FIG. 3—Shows results of rapamycin treatment of human keratinocytes. FIG. 3A Panel 1 shows results by western blot analysis of the effect on K6 expression in human keratinocyte cells when treated with increasing concentrations of rapamycin and harvested. FIG. 3A Panel 2 shows quantitated values (from Panel 1) of K6a expression in human keratinocyte cells plotted against rapamycin concentrations. FIG. 3b Panel 1 shows a timecourse analysis of effect of rapamycin on the human keratinocyte. FIG. 3b Panel 2 shows quantitated values (from Panel 1) of the K6a expression in human keratinocyte cells treated with rapamycin overtime.

FIG. 4—Shows treatment with rapamycin results in clinical improvement in three pachyonychia congenita patients. FIG. 4B shows results from The Dermatology Life Quality Index (DLQI) questionnaire which was utilized to assess the impact of rapamycin treatment on daily activities. The Y-axis DLQI data is inverted to allow easier visualization of increased quality of life. DLQI and trough levels are correlated (insert).

DETAILED DESCRIPTION OF EXAMPLE EMBODIMENT(S)

Figure 1:
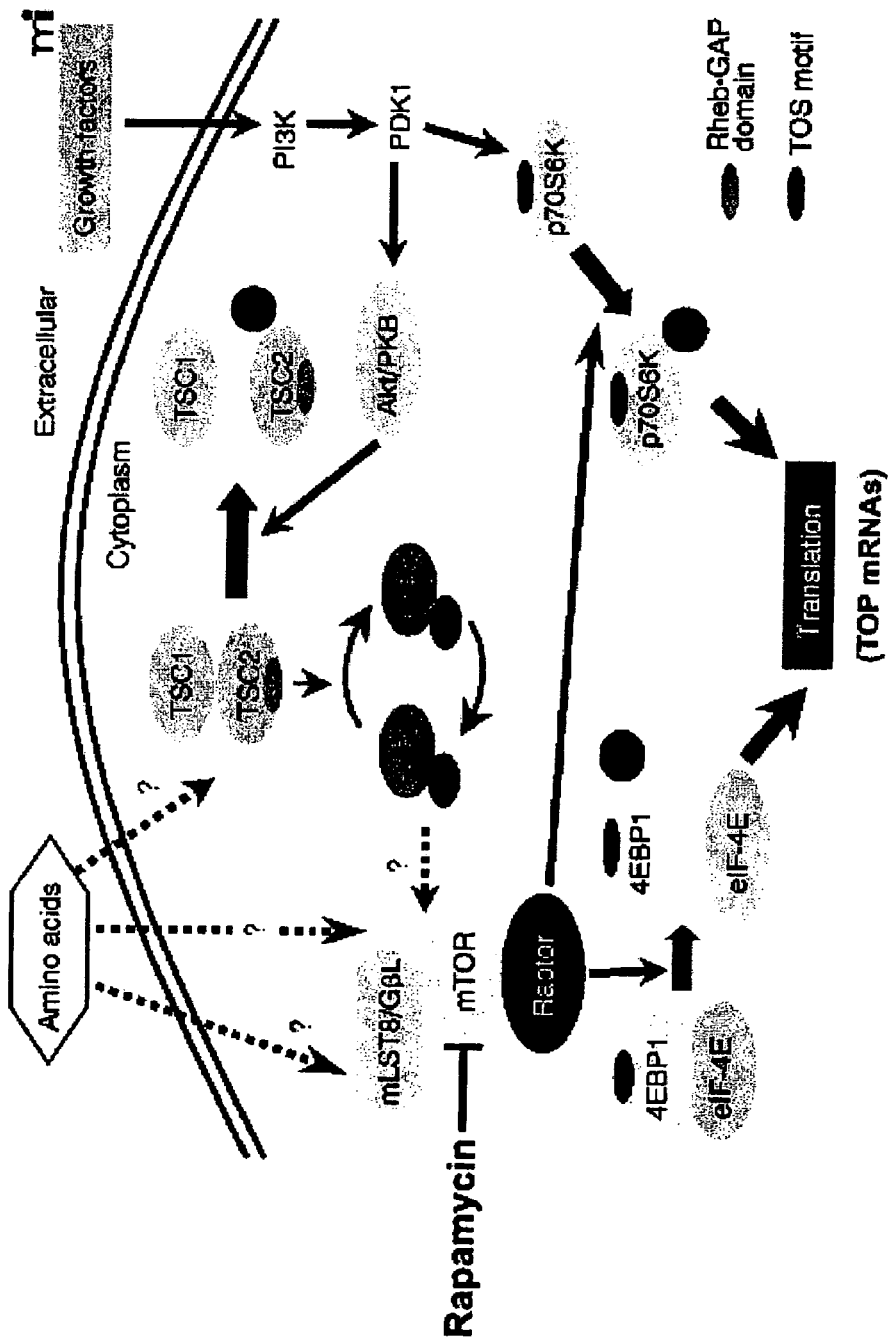
FIG. 1—Shows an overview of mTOR signaling in mammals (figure modified from K. Yonezawa, Mol Interv., 2003). The mammalian target of rapamycin (mTOR) is a key modulator of signal transduction leading to efficient translation of certain classes of messenger RNAs including those that contain a terminal oligopyrimidine (TOP) regulatory motif. In the proposed model, rapamycin blocks signal transduction by binding to mTOR resulting in decreased translation of TOP mRNAs (including K6a according to the model proposed here) at the level of ribosome initiation, resulting in decreased K6a protein synthesis.

Reference will now be made to the exemplary embodiments illustrated, and specific language will be used herein to describe the same. It will nevertheless be understood that no limitation of the scope of the invention is thereby intended.

As used herein, "subject" refers to a mammal having a keratin hyperproliferation disorder. In some aspects, such subject may be a human.

The term "keratin hyperproliferation disorders" refers to skin disorders in which the inducible keratins, K6a, K6b, K16, and K17, are overexpressed or inappropriately expressed. Non-limiting examples of such disorders include keratosis pilaris (including follicular hyperkeratosis), pachyonychia congenita, hyperhidrosis, warts, and calluses. Another example of such a skin disorder is psoriasis.

The term "mTOR inhibitor" refers to agents or compounds which are effective in inhibiting mTOR or an inhibitor of the mTOR signaling pathway. mTOR is a serine/threonine kinase that regulates translation and cell division. Examples of mTOR inhibitors include but are not limited to rapamycin (sirolimus) and its analogues and derivatives, temsirolimus, everolimus, the rapamycin prodrug AP-23573, AP-23481, the like, and combinations thereof.

As used herein, the term "inhibition of" or "silencing of" with respect to genetic expression refers to the absence of, or at least an observable decrease in, the level of protein (or protein activity) from a target gene.

As used herein, "effective amount" or "therapeutically effective amount" of a inhibitory agent refers to a sufficient amount of inhibitory agent to perform an intended task and achieve an intended result. For example, an effective amount of rapamycin may be an amount which is sufficient to silence expression a keratin gene. It is understood that various biological factors may affect the ability of a particular agent to perform its intended task. Therefore, an "effective amount" or a "therapeutically effective amount" may be dependent in some instances on such biological factors. Further, while the achievement of therapeutic effects may be measured by a physician or other qualified medical personnel using evaluations known in the art, it is recognized that individual variation and response to treatments may make the achievement of therapeutic effects a somewhat subjective decision. The determination of an effective amount is well within the ordinary skill in the art of pharmaceutical sciences and medicine.

As used herein, sequences, compounds, formulations, delivery mechanisms, or other items may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 0.5 to 10 g" should be interpreted to include not only the explicitly recited values of about 0.5 g to about 10.0 g, but also include individual values and sub-ranges within the indicated range. Thus, included in this numerical range are individual values such as 2, 5, and 7, and sub-ranges such as from 2 to 8, 4 to 6, etc. This same principle applies to ranges reciting only one numerical value. Furthermore, such an interpretation should apply regardless of the breadth of the range or the characteristics being described.

Unless otherwise defined, all technical and scientific terms used herein have the same meaning as commonly understood to one of ordinary skill in the art to which this invention belongs. Although any methods, devices and materials similar or equivalent to those described herein can be used in the practice or testing of the invention, representative methods, devices, and materials are described below.

It has been discovered that the expression of the inducible keratins containing a translation regulatory motif (e.g. K6a and K17 and likely K6b and K16) can be selectively inhibited by mTOR inhibitors. Inappropriate expression of these keratins appears to be involved in a number of hyproliferation skin disorders including but not limited to psoriasis, keratosis pilaris, pachyonychia congenita, hyperhidrosis, warts, and calluses. It is believed that the mTOR inhibitors are effective against these inducible keratins because the mRNAs encoding these keratins contain within their 5' untranslated regions translation regulatory sequences that usually begin with a "c" residue, followed by a track of pyrimidines ("c" or "u" residues) ranging from 4-14 nucleotides. Messenger RNAs having this type of initiation sequence are referred to as terminal oligopyrimidine (or TOP) mRNAs.

In one embodiment of the present invention, a method of treating or preventing keratin hyperproliferation disorder is proposed. The method includes administering an amount of mTOR inhibitor to a subject suffering with a keratin hyperproliferation disorder. The mTOR inhibitors which can be used in the present invention include but are not limited to rapamycin (sirolimus) and its analogues and derivatives, temsirolimus, everolimus, the rapamycin prodrug AP-23573, AP-23481, and combinations thereof. In one embodiment the mTOR inhibitor is rapamycin. In another embodiment mTOR inhibitor is a combination of rapamycin and a second mTOR inhibitor.

The mTOR inhibitor can be administered in any method or mode known in the art, including oral, topical, injection, and transdermal administration. In one embodiment the mTOR inhibitor is administered transdermally. In another embodiment the mTOR inhibitor is administered orally. When the mTOR inhibitor is administered orally, it can be administered in an amount of from 2 mg/day to 20 mg/day. In one embodiment, the oral administration can be formulated to be delivered in a single oral dosage form. In another embodiment, the mTOR inhibitor can be administered via injection or intravenously. Administration by injection can be done at or near an area in which the keratin hyperproliferation is manifested. In another embodiment the mTOR inhibitor can be administered topically. In some situations it may be desirable to administer the mTOR both orally and either topically or transdermally. For example, in one embodiment, the mTOR inhibitor can be administered orally and transdermally. When the mTOR inhibitor is administered orally and by another method, the mTOR inhibitor administered orally can be the same or different than the mTOR inhibitor administered by the other method.

The treatment of a subject experiencing a keratin hyperproliferation disorder using an mTOR can reduce or eliminate symptoms and/or signs associated with the keratin disorder. In one embodiment, the treatment using the mTOR inhibitor can provide a reduction of a pain scores as measured by the Dermatology Life Quality Index (DLQI) (see Example 4) or other appropriate evaluation known in the art.

Example 1 mTOR Signaling in Mammals

Regulation of inducible keratin gene expression is believed to occur post-transcriptionally, likely at the level of mRNA translation. Functional K6 and K16 mRNAs are found throughout normal epidermis but are not translated into protein. As most translational regulation is mediated through 5' untranslated motifs (the inducible keratins may be regulated in a coordinate fashion), we performed a sequence comparison using published keratin mRNA sequences as well as genomic sequences. The transcriptional start site for human K6a was mapped by primer extension to a "C" residue, which is imbedded in a tract of 21 pyrimidines. The putative resulting transcript had seven pyrimidines at the 5' end. Terminal oligopyrimidine (TOP) regulatory motifs (4-14 pyrimidines adjacent to 5' cap site, are known to be responsible for regulation of a class of mRNAs (TOP mRNAs) at the level of mRNA translation in a growth-dependent fashion. Treatment with the macrolide rapamycin (sirulimus) was shown to specifically down-regulate TOP mRNA translation. Rapamycin binds to and inhibits mTOR (Mammalian target of rapamycin), resulting in inactivation of p70 S6 kinase ($p70^{S6K}$) and activation of eIF-4E binding protein 1 (4EBP1), leading to decreased translation of TOP mRNAs. FIG. 1 shows the mTOR signaling pathway in mammals.

Example 2

Comparison of Untranslated Regions of Keratins K6a, K6b, K16, and K17

A comparison of the 5' untranslated regions of the inducible keratins (K6a, K6b, K16, and K17) publicly available in the NCBI GenBank database (www.ncbi.nlm.nih.gov/Genbank) identified human and murine K6a as well as human K17 as TOP mRNAs, each initiating with a "c" residue and containing the consensus oligopyrimidine tract at the 5' terminus (see FIG. 2). It is likely that the other inducible keratins also contain this element as their expression may be regulated in a coordinate fashion. The lack of a TOP element for human K6b and K16 likely reflects that the 5' untranslated regions of mRNAs are often not mapped accurately. As an example, immediately upstream of the reported 5' terminus of K6b exists an oligopyrimidine track, within which is likely the initiation site of the mRNA (see FIG. 2). Furthermore, there is a pyrimidine motif consisting of 14 continuous "u" and "c"

residues in the middle of the 5' UTR of human K16, within which transcription may occur.

Example 3

Rapamycin Treatment of Human Keratinocytes

In order to test the hypothesis that inducible keratins are members of the TOP mRNA family, human HaCaT keratinocytes were treated with rapamycin. In one portion of the experiment, HaCaT cells were treated with increasing concentrations of rapamycin and harvested at 96 h and the effect on K6 expression was monitored by western blot analysis. (FIG. 3A, Panel 1). Rapamycin effectively inhibited expression of the K6 keratin, with little or not effect on a control (Lamin A/C). As shown in FIG. 3A Panel 2, K6a expression was indeed inhibited in a dose dependent fashion at low rapamycin concentrations (IC50 of ~1 nM).

A timecourse analysis of effect of rapamycin on the HaCaT keratinocytes was also performed. The HaCaT keratinocytes were treated with 10 nM rapamycin and harvested over a range of time points. At the indicated times, cells were harvested and lysed in SDS-PAGE loading buffer, subjected to denaturing SDS-PAGE analysis and electroblotted to nitrocellulose. (FIG. 3B, Panel 1). K5, K6, and K14 expression were detected by specific antibodies and visualized by the NBT/BCIP system. The timecourse analysis revealed that inhibition begins at about 36 h post-treatment and persists for at least 144 h (see FIG. 3B, panel 2).

Example 4

Clinical Testing of Rapamycin in Subjects with Pachyonychia Congenita

A small number (n=3) of pachyonychia congenita patients, one female (IPCRR #10) with the K6a(N171K) mutation and two male PC patients (IPCRR #2 and #11) with the K16 (N125D) mutation were identified through the International Pachyonychia Congenita Research Registry (www.pachyonychia.org). These patients were invited to participate in a three to five month off-label use of oral rapamycin (Rapamune®, Wyeth Pharmaceuticals, Inc.). Rapamycin was given in the standard fashion following typical recommendations for use as an adjunct therapy in renal transplantation. Prior to initiation of therapy a pregnancy test was performed in the female patient (she was on oral contraceptive prophylaxis) and all three patients received a pre-therapy evaluation including: cbc, CMP (sodium, potassium, chloride, carbon dioxide, anion gap, BUN, creatinine, glucose, ALT, AST, calcium, total protein, albumin, bilirubin), lipid panel (cholesterol, triglycerides, HDL, LDL, VLDL), UA with microanalysis, PA and lateral chest x-ray. The starting dose was 2 mg per day and trough levels were obtained at steady state after 2 weeks. The dosage was increased every two weeks until trough levels reached a range of 9-12 ng/mL. Patients were re-evaluated for effects and side effects every two weeks and photographs of plantar calluses were taken to document their progress.

Laboratories were performed which included: rapamycin trough level, UA with microanalysis, cbc with differential, CMP, lipid panel, pregnancy test (patient 10 only). Under the same WIRB protocol, patients also completed a daily pain diary rating their level of pain on a scale of 1-10 several times per day and a bi-weekly well-validated life quality evaluation (DLQI) at the time of their clinic visit. The patient with the K6a mutation collected callus shavings during her usual grooming routine prior to, during, and after treatment with rapamycin. The shavings were placed immediately in RNALater (Ambion) and RNA was extracted for future quantitative real-time quantitative PCR (RT qPCR) analysis of keratin expression.

Figure 4A:
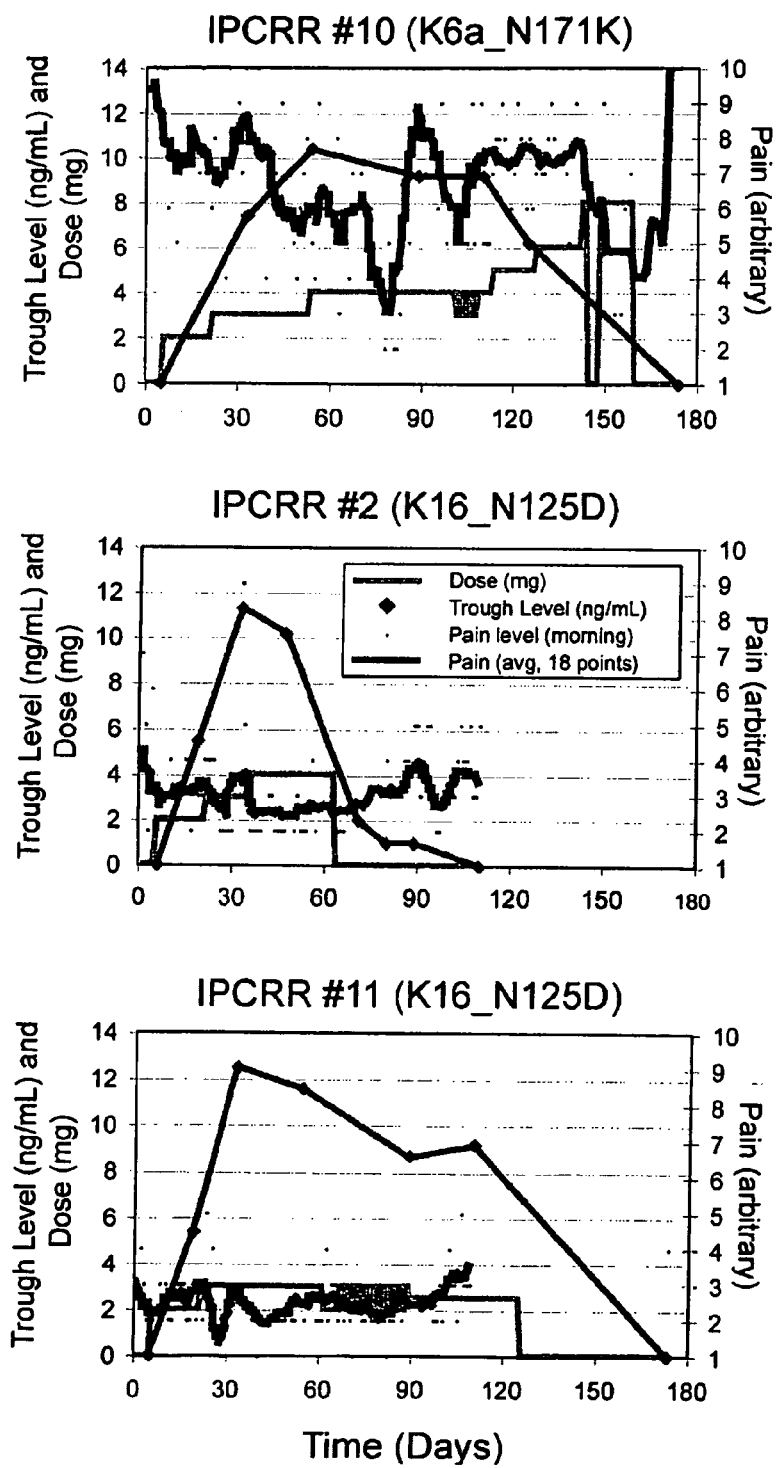
FIG. 4A shows pain measures, based on arbitrary pain levels on a 1-10 scale (10 most painful), reported as either the morning level (upon waking-therefore not as heavily influenced by daily activity (dots) or the running average of morning pain levels reported (18 datapoints averaged, line).

Patient reported pain (morning assessment) and DLQI quality of life scores were plotted over time and with respect to dose of drug received and trough level over that time period. (see FIGS. 4A and 4B). Patients IPCRR #10, 2, and 11 received rapamycin for 156, 109, and 56 days, respectively, with maximal trough levels of 10.4, 12.5, and 11.3 ng/mL, respectively, and with maximal doses of 8 mg/day, alternating 2 mg and 3 mg on consecutive days, and 4 mg/day, respectively. All patients experienced a side effect that ultimately resulted in discontinuation of use of the drug. Patient 10 developed diarrhea and aphthous ulcers, patient 2 developed gastrointestinal distress with loss of appetite, and patient 11 developed an acneiform follicular eruption. None of the patients experienced any laboratory abnormalities or serious side effects. Significantly, in spite of these side effects arising from systemic administration of rapamycin, all three patients reported an increased quality of life (as reflected by decreasing DLQI score, note inverted axis in FIG. 4B) that paralleled the rapamycin trough level. As might be expected, the subjective pain scale was more variable than the DLQI scores, but as a general trend, the lower pain scores corresponded to higher trough levels. Of particular note for patient 10 is the discontinuation of rapamycin (days 145-148 due to concerns regarding diarrhea while traveling) during which time a trough level was not obtained. This period was associated with high level of pain followed by decrease of pain level when drug treatment was re-initiated and assumed to reach therapeutic levels (trough level was not obtained). The simple pain scale used in this study was not as good as the DLQI in adequately capturing the overall subjective experience of pain in these patients, especially patients 2 and 11. Both of these patients reported that they felt their pain was improved, but the pain scores did not reflect their general impression. These patients reported that this was due in part to the increased level of activity that spontaneously occurs when pain decreases. An improved pain scale is currently under development, which incorporates activity level into the subjective reporting system.

Figures 4C, 4D:
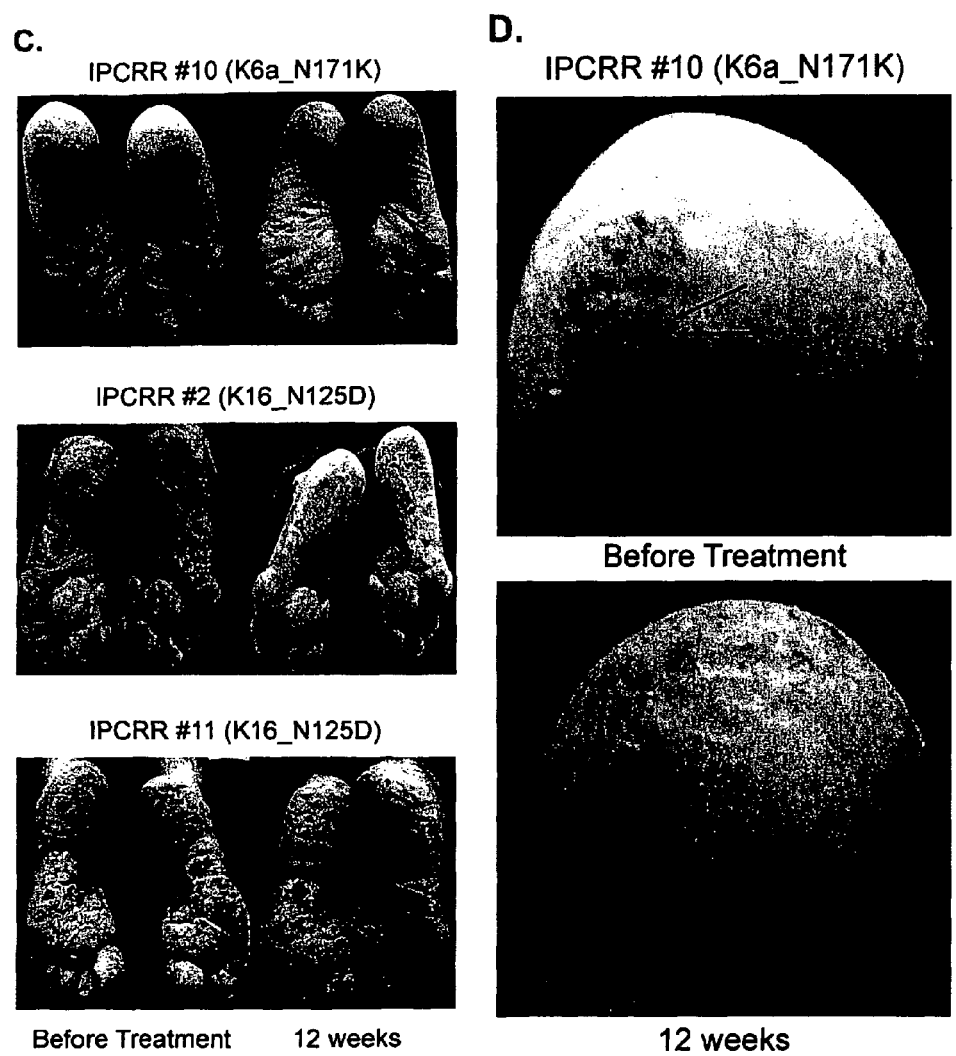
FIG. 4C shows photographic before-and-after images of plantar hyperkeratosis, blisters and neurovascular structures.
FIG. 4D shows magnification of the heel region of patent IPCRR #10 from FIG. 4C containing the neurovascular structures. Specifically, it shows how the rapamycin treatment resulted in the reduction or resolution of these painful regions (see arrows). The reduced hyperkeratosis observed may be at least partially due to the ability of the patient to trim calluses much deeper due to receding neurovascular structures and the associated decreased pain.

In addition to subjective improvement of plantar pain and improved quality of life, patients also demonstrated important clinical changes in the plantar calluses. FIG. 4C shows photographs taken of the plantar keratoderma before initiation of systemic rapamycin therapy and 12 weeks into the treatment course. The photographs demonstrate decreased keratoderma following treatment, particularly in the K6a PC patient. Of note, this patient has long noted that the level to which she is able to remove callus is determined by the level at which the blade reaches capillaries and associated pain fibers. At the 12 week time point, the depth at which these neurovascular structures were found appeared to be regressed relative to baseline (see FIG. 4D).

Example 5

Treatment of Keratin Hyperproliferation using Temsirolimus

A subject suffering from a keratin hyperproliferation disorder is administered a therapeutically effective oral dose of temsirolimus (TORISEL™) for a period of about 120 days. During the time of treatment, the subject's pain and kerato derma associated with the keratin hyperproliferation disorder are reduced.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. A method of treating or preventing a keratin hyperproliferation skin disorder in a subject resulting from overexpression or inappropriate expression of a keratin encoded for by an mRNA having a terminal (TOP) motif, comprising:
    administering to the subject a therapeutically effective amount of an mTOR inhibitor, selected from the group consisting of rapamycin, rapamycin prodrugs, rapamycin derivatives, and combinations thereof;
    wherein the keratin hyperproliferation skin disorder is selected from the group consisting of keratosis pilaris, pachyonychia congenita, hyperhidrosis, warts, and calluses.

2. A method as in claim 1, wherein the mTOR inhibitor is rapamycin.

3. A method as in claim 1, wherein the keratin hyperproliferation skin disorder is keratosis pilaris.

4. A method as in claim 1, wherein the keratin hyperproliferation skin disorder is pachyonychia congenita.

5. A method as in claim 1, wherein the administration of said mTOR inhibitor is oral.

6. A method as in claim 5, wherein the mTOR inhibitor is administered in an amount of from 2 mg/day to 20 mg/day.

7. A method as in claim 1, wherein the administration of said mTOR inhibitor is topical.

8. A method as in claim 1, wherein the administration of the mTOR inhibitor is transdermal.

9. A method as in claim 1, wherein the administration of the mTOR inhibitor is both oral and topical.

10. A method as in claim 1, wherein said overexpressed or inappropriately expressed keratin is selected from the group consisting of K6a, K6b, K16, and K17.

11. A method as in claim 1, wherein the administration of the mTOR inhibitor provides for a reduction in DLQI measured pain scores for the subject.

12. A method as in claim 1, wherein the mTOR inhibitor is a rapamycin derivative selected from the group consisting of temsirolimus, everolimus, or a combination thereof.

13. A method as in claim 1, wherein the mTOR inhibitor is a rapamycin prodrug selected from the group consisting of AP-23573, AP-23481, or a combination thereof.

* * * * *